(12) United States Patent
Chaudhuri

(10) Patent No.: US 12,017,025 B1
(45) Date of Patent: Jun. 25, 2024

(54) NON-DISPOSABLE LIQUID DISPENSING DEVICE

(71) Applicant: Sid Chaudhuri, East Brunswick, NJ (US)

(72) Inventor: Sid Chaudhuri, East Brunswick, NJ (US)

(*) Notice: Subject to any disclaimer, the term of this patent is extended or adjusted under 35 U.S.C. 154(b) by 0 days.

(21) Appl. No.: 18/097,334

(22) Filed: Jan. 16, 2023

(51) Int. Cl.
*A61M 3/02* (2006.01)
*B65D 47/20* (2006.01)
*B65D 83/00* (2006.01)

(52) U.S. Cl.
CPC ........ *A61M 3/0245* (2013.01); *A61M 3/0233* (2013.01); *A61M 3/0279* (2013.01); *B65D 47/20* (2013.01); *B65D 83/0022* (2013.01)

(58) Field of Classification Search
CPC ........ A61M 5/20; A61M 5/24; A61M 5/3202; A61M 3/02; A61M 3/0279; A61M 3/0233; A61M 3/0245; A61M 3/0254; A61M 3/0258; A61M 3/0262; A61M 2005/2403; A61M 2005/2444; A61M 2005/208; B65D 83/005; B65D 83/0022; B65D 83/0033; B65D 83/0044
See application file for complete search history.

(56) References Cited

U.S. PATENT DOCUMENTS

| 5,092,842 | A | * | 3/1992 | Bechtold | A61M 5/20 604/209 |
| 5,373,971 | A | * | 12/1994 | Laffy | B65D 83/0022 222/320 |
| 5,626,566 | A | * | 5/1997 | Petersen | A61M 5/31585 604/211 |
| 6,248,095 | B1 | * | 6/2001 | Giambattista | A61M 5/31551 604/207 |

* cited by examiner

*Primary Examiner* — Laura A Bouchelle
*Assistant Examiner* — Hong-Van N Trinh

(57) ABSTRACT

The present invention provides a liquid dispensing device made of non-plastic material for its use to squirt liquid through a nozzle of the device. The non-disposable device is an environmentally friendly and health safe alternative to conventional plastic bottles used by millions of people suffering from allergies for nasal irrigation. The device comprises a main body structure including a plunger disc, a push button operation mechanism, a container, and a nozzle. The container is detachable from the main body so it can be filled with water and warmed up in a microwave oven. When the button is pushed to plunge the disc into the container, warm water is squirted through the nozzle into a nasal opening.

15 Claims, 15 Drawing Sheets

NON-DISPOSABLE LIQUID DISPENSING DEVICE

FIELD OF THE INVENTION

This invention generally relates to bottles from which liquid can be squeezed out. Such bottles are used for many different purposes. One ubiquitous use is for nasal irrigation to alleviate sinus congestion arising from allergy or infection. Nasal irrigation bottles currently available in the market are made of plastic. These bottles are squeezed by hand to push warm saline water from the bottles into the nasal openings. The bottles according to the current invention are non-plastic, non-disposable, health-safe, environmentally friendly, and easy to use.

BACKGROUND OF THE INVENTION

This invention relates to a liquid dispensing device that is operated by hand to squeeze liquid out of a nondeformable solid container at any desired pressure by applying appropriate amount of push on a handle or a push button provided in the device according to the current invention.

Plastic squeeze bottles are used for many different applications. One important application is for nasal irrigation currently used by millions of people suffering from allergy to alleviate nasal congestion.

A plastic nasal irrigation bottle comprises two parts. One part is a plastic squeezable bottle with a neck and a thread on the neck. The second part is a nozzle with a tube attached to the nozzle. The upper part of the nozzle is protruded such that its outer surface fits snugly onto a nasal opening. The nozzle is threaded into the liquid filled bottle. While holding the bottle with its nozzle snugly fit onto a nasal opening, the bottle is squeezed to push warm saline water from the bottle into the nasal passage. The plastic bottle is typically placed in a microwave oven to warm up the saline water in it.

A plastic nasal irrigation bottle is a simple and easy-to-use device. However, there are several deficiencies. The bottle must be thrown away after using it for a short period of time. Typical recommended replacement period is three months. The primary reason for replacing a plastic bottle is that plastic material frays and more chemicals leach into the liquid more it is used causing adverse health effects. Second, even with recycling, plastic bottles are not environmentally friendly. The production of millions of disposable plastic bottles adversely impacts the environment.

Thus, there is a need for a liquid dispensing device that is completely health safe, non-disposable, environmentally friendly, and easy to use.

SUMMARY OF THE INVENTION

The present invention provides a liquid dispensing device and a method for its use to squeeze liquid out of the device; wherein the container of the device is non-disposable. The device according to this invention can be used for nasal irrigation.

In accordance with the present invention, a liquid dispensing device comprises a liquid container, a main body subsystem, an operation subsystem, and a nozzle. The container is made of non-plastic, non-disposable solid material and preferably of cylindrical shape. The top end of the container has a thread on the outside so it can be threaded onto the main body subsystem. The main body subsystem allows the container to be inserted into, to be held securely, and removed out of the main body subsystem. The container is inserted into and threaded onto the main body subsystem. The material of the container is chosen for it to be safe to be used in a microwave oven or a conventional oven to heat up the liquid in the container. The container material being non-plastic, it can be selected to be completely health safe.

The main body subsystem comprises a lid subsystem, a base subsystem, and a support structure to hold the lid subsystem, the base subsystem, and the container. The support structure is a set of posts connecting the base at the bottom of the main body subsystem and a ring at the top of the main body subsystem. The support structure includes at least one opening through which the container is inserted into or removed out of the main body subsystem.

The operation subsystem comprises a rod, a hollow structure, a plunger disc, and a button. The rod is preferably U-shaped. The rod couples the button at one end and the plunger disc at the other end of the U-shaped rod. The plunger disc is of a shape and size to substantially fit and to slide through the inner wall of the container in a liquid-tight manner when the plunger disc is pushed into the container. When the button is pushed down, the plunger disc being connected by the rod is also pushed down into the container. At least a portion of the button and at least a portion of the rod slides through the hollow structure when the button is pushed.

The lid subsystem comprises a lid wherein the lid has a first thread on the inside of the lid matching a thread on the outside of the container allowing the lid to be threaded onto the container. The lid includes a neck at the top part of the lid wherein the neck comprises a second thread at the outside of the neck. The second thread is matching with a thread on the nozzle allowing the nozzle to be threaded securely onto the lid. The lid includes a hole to allow a rod of the operation subsystem to pass through the hole.

The nozzle comprises a head and a tube. The tube is attached to the head so that there is a hole through the nozzle from top to bottom. The shape of the head is designed for its outer surface to fit snugly onto a nasal opening for the nasal irrigation application. The nozzle tube is designed to be of length approximately equal to the container height but leaving a small space at the bottom so liquid from the container can be pushed up the tube. The nozzle has a thread on the inside of the head for it to be threaded onto the neck of the lid.

The base subsystem comprises a solid or a hollow disc and a spring holding structure placed at the periphery of the base. A spring is held inside the spring holding structure. Two latches are attached to the two ends of the spring. When the container is inserted into the main body subsystem through the two latches, the springs hold the container on the base securely. The spring structure can alternatively be placed at the top or the middle portion of the support structure.

When the liquid filled container is inserted into the main body subsystem, the container is threaded onto the lid subsystem, and the nozzle is threaded onto the lid subsystem, the device is ready for operation.

While holding the outer surface of the head of the nozzle snugly onto a nasal opening, the button is pushed down. The rod attached to the button pushes the plunger disc down the container. Being squeezed down by the plunger disc, water is pushed up through the tube of the nozzle into the nasal opening. The flow of water into the nose is controlled by adjusting the amount of push.

DETAILED DESCRIPTION

Figure 1:
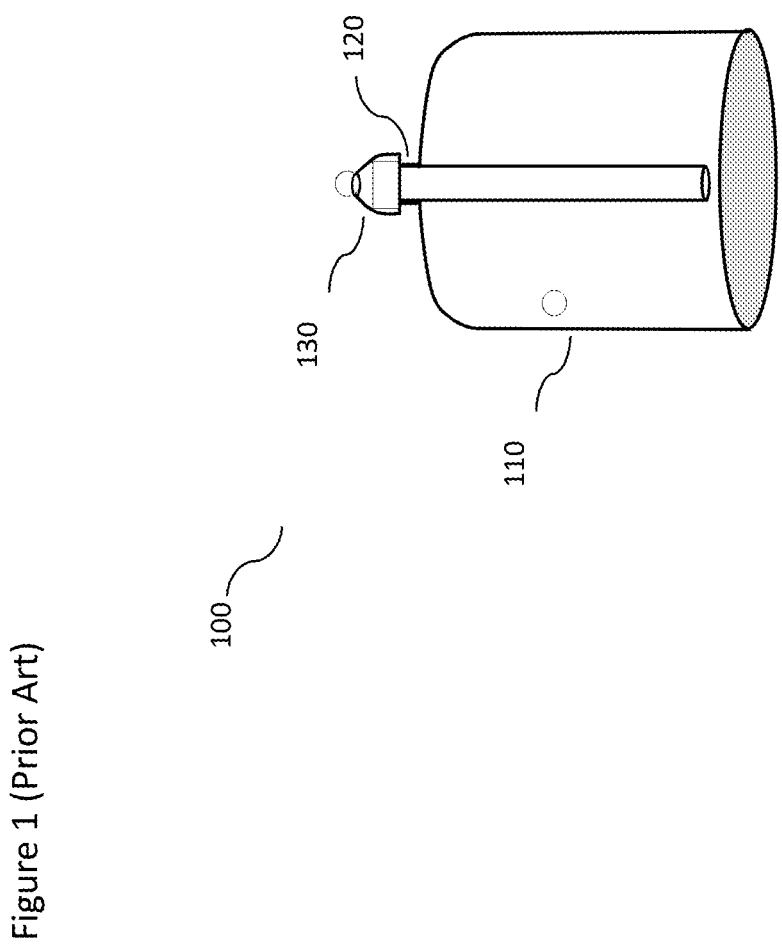
FIG. 1 depicts a schematic diagram of the salient components of a conventional liquid dispensing bottle.

FIG. 1 depicts the salient components of a conventional liquid dispensing bottle 100. The bottle comprises a liquid container 110 and a nozzle 130. The neck 120 of the container 110 has a thread on the outside. The nozzle comprises a head and a tube with a hole that are connected to each other as shown. The outer surface of the head is shaped so it fits snugly in the opening of a nose. The head has a thread (not shown) on the inside of its bottom part so it can be threaded onto the thread of the neck 120.

Figure 2:
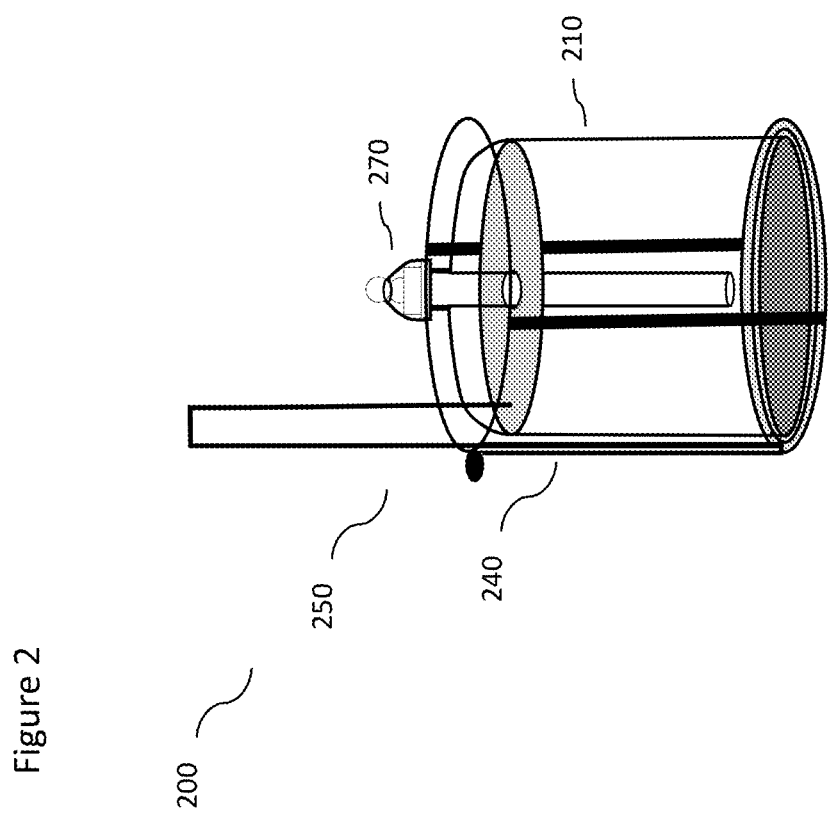
FIG. 2 depicts a schematic diagram of a liquid dispensing apparatus in accordance with the current invention.

FIG. 2 depicts a schematic diagram of the salient components of a liquid dispensing apparatus generally designated as 200 in accordance with the current invention. The apparatus comprises a container 210, a main body subsystem 240, an operation subsystem 250, and a nozzle 270. The container 210 filled with liquid is inserted into the main body subsystem 240 horizontally from a side of the main body subsystem 240; the nozzle 270 is threaded at an upper section of the main body subsystem 240; and the container 210 is threaded at a lower section of the main body subsystem 240 when liquid is to be dispensed from the container by operating the main body subsystem 240 of the apparatus 200.

Figure 3:
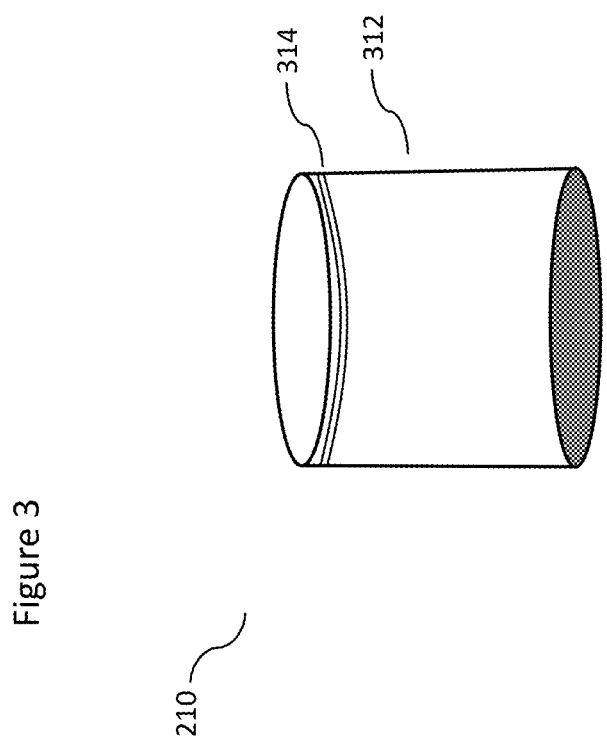
FIG. 3 depicts a schematic diagram of the container of the apparatus in accordance with the current invention.

FIG. 3 depicts a schematic diagram of the container 210 of the apparatus. The container 210 is a solid container 312 having threads 314 on the outer side of the top part of the container for it to be threaded onto the main body subsystem 240. The shape of the container 312 is preferably cylindrical. The container can be of other shapes, e.g., the horizontal cross-section of the container is polygonal such as square, hexagonal, octagonal, etc. or an ellipse. The container is made of non-disposable and microwave safe material such as ceramic, glass, silicone, and plant-based plastic. The material can also be selected so it can be used to heat up liquid directly on an electrical or gas cook top such as aluminum and stainless steel. The size of the container is suitably designed to hold appropriate amount of liquid for the application such as nasal irrigation.

Figure 4:
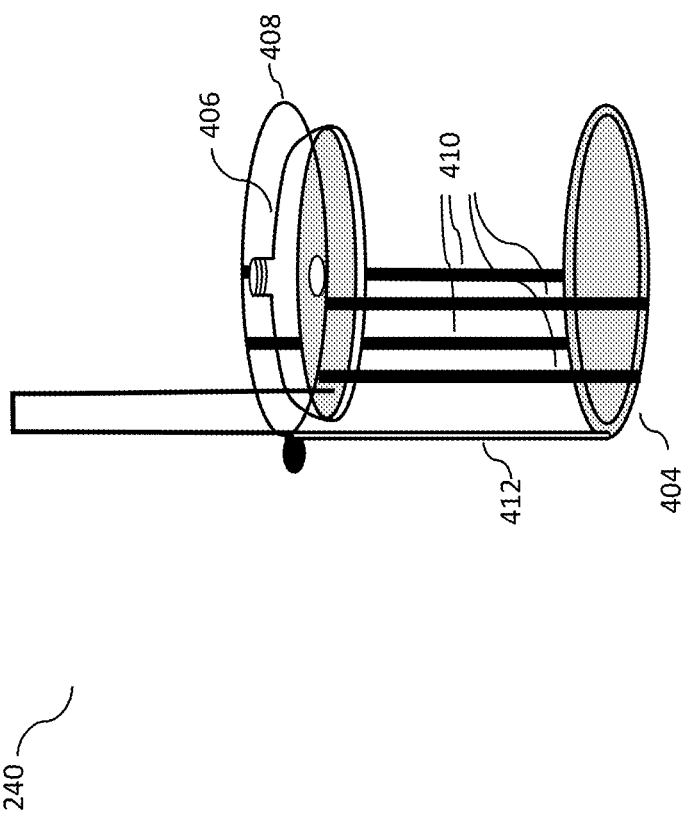
FIG. 4 depicts a schematic diagram of the main body subsystem of the apparatus in accordance with an embodiment of the current invention.

FIG. 4 depicts a schematic diagram of the main body subsystem 240 of the apparatus in accordance with an embodiment of the current invention. The subsystem 240 comprises a base subsystem 404, a lid subsystem 406, an annular ring 408, multiple posts 410, and a hollow post structure 412. The posts 410 connect the ring 408 and the base subsystem 404 at the top and at the bottom of the posts, respectively. The number of posts and locations are selected for appropriate structural strength of the main body subsystem 240. The main body subsystem 240 is designed so that the opening between the two rightmost posts allows easy insertion and removal of the container 210 into and out of the main body subsystem 240. In an alternative embodiment, the ring 408 is a disc with a hole in the middle.

Figure 5:
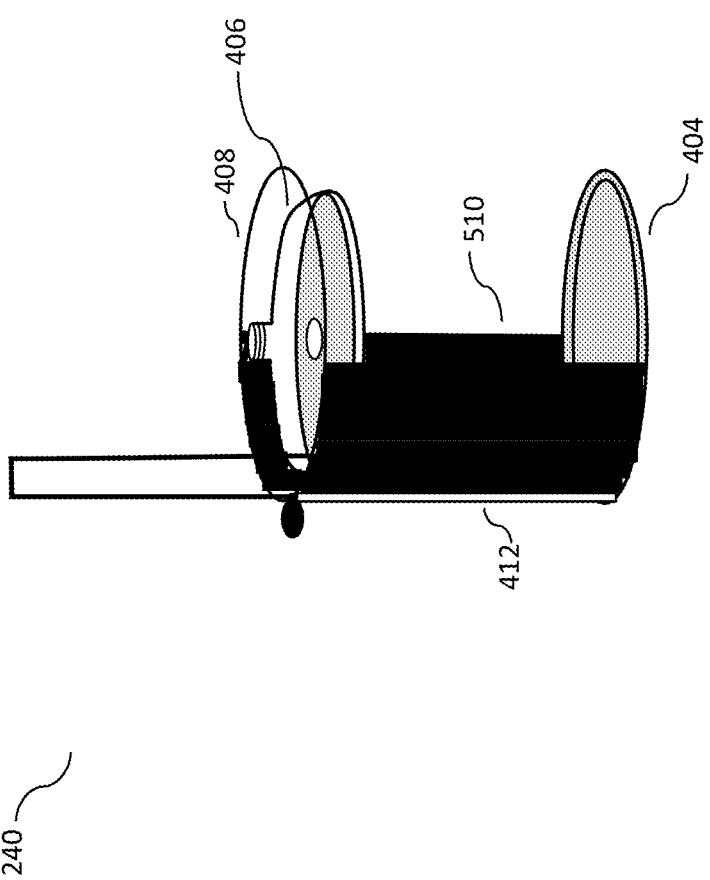
FIG. 5 depicts a schematic diagram of the main body subsystem of the apparatus in accordance with another embodiment of the current invention.

FIG. 5 depicts a schematic diagram of the main body subsystem 240 of the apparatus in accordance with another embodiment of the current invention. In this embodiment, the posts 410 are replaced with a sheet 510 surrounding a portion of the main body subsystem 240. The sheet 510 connects the ring 408 and the base 404 together and provides the structural support for the main body subsystem 240. The sheet 510 includes an opening on the right-hand side for the container 210 to be inserted into and removed out of the main body subsystem 240.

Figure 6:
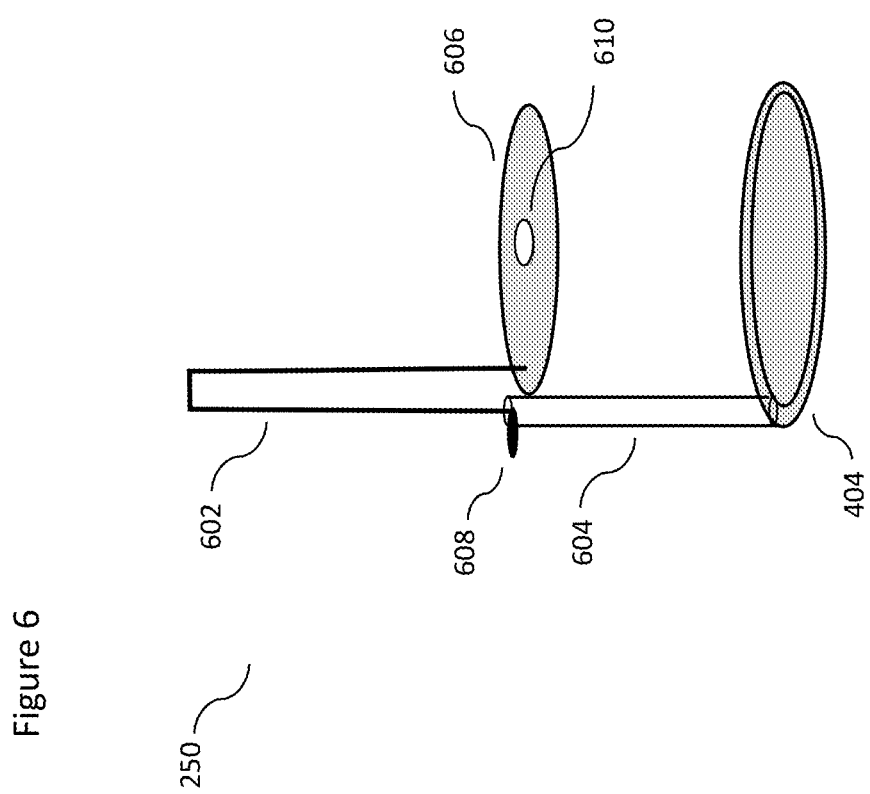
FIG. 6 depicts a schematic diagram of the operation subsystem of the apparatus in accordance with an embodiment of the current invention.

FIG. 6 depicts a schematic diagram of the operation subsystem 250 of the apparatus in accordance with an embodiment of the current invention. The operation subsystem 250 comprises a U-shaped rod 602, a tube 604, a plunger disc 606, and a push button 608. One end of the rod 602 is attached to the plunger disc 606 and the other end of the rod 602 is attached to the push button 608. The plunger disc 606 is designed so it fits snugly on the inner surface of the container 312 in a watertight manner. The plunger disc 606 can be fitted with a rubber ring at the outer edge, so it is watertight when pushed inside the container 312. The tube 604 is hollow and there is a slit or opening on the left-hand side of the tube 604 so the left-hand arm of the U-shaped rod 602 and a portion of the button 608 can go up or down the tube 604 when the button 608 is pushed up or down. The structure 604 can alternatively be a post. In this case the button with a hole slides through the post. The plunger disc 606 includes a hole 610 for a tube of the nozzle to slide through the hole in a watertight manner. The U-shaped rod 602 and the button 608 constitute a lever device that is used to push the plunger disc 606 inside the container 312.

Figure 7:
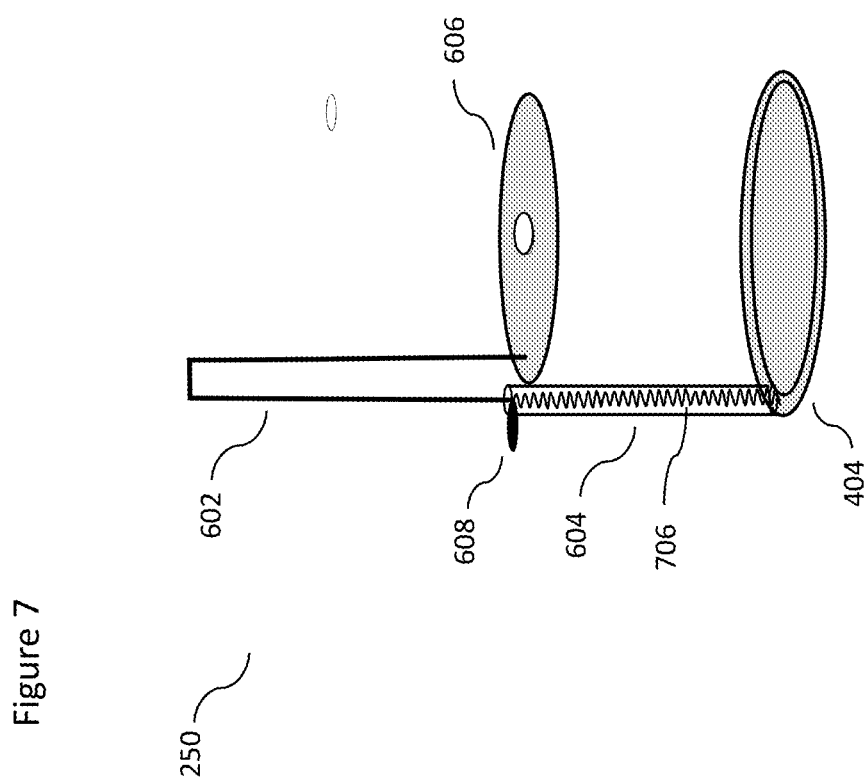
FIG. 7 depicts a schematic diagram of the operation subsystem of the apparatus in accordance with another embodiment of the current invention.

FIG. 7 depicts a schematic diagram of the operation subsystem 250 of the apparatus in accordance with another embodiment of the current invention. In this embodiment, there is a spring 706 inside the tube 604 in addition to the components shown in FIG. 6. The upper end of the spring 706 is attached to the bottom of the button 608 and the lower end of the spring is attached to the upper side of a disc in the base subsystem 404. A latch (not shown) is provided at the bottom of the spring so that when the button 608 is pushed all the way down the spring is snapped onto the latch and the button 608 and the left arm of the U-shaped rod 602 stay pushed down into the tube 604. When the apparatus is to be used again the button 608 is pushed upwards causing the latch to open and letting the button 608 and the rod 602 to move upwards. The apparatus is then ready for operation. In this embodiment of the operation subsystem 250, the rod 602 does not need to be held up for the container 210 to be inserted into the main body subsystem 240. Instead, the spring 706 holds up the plunger disc 606 and the rod 602.

Figure 8:
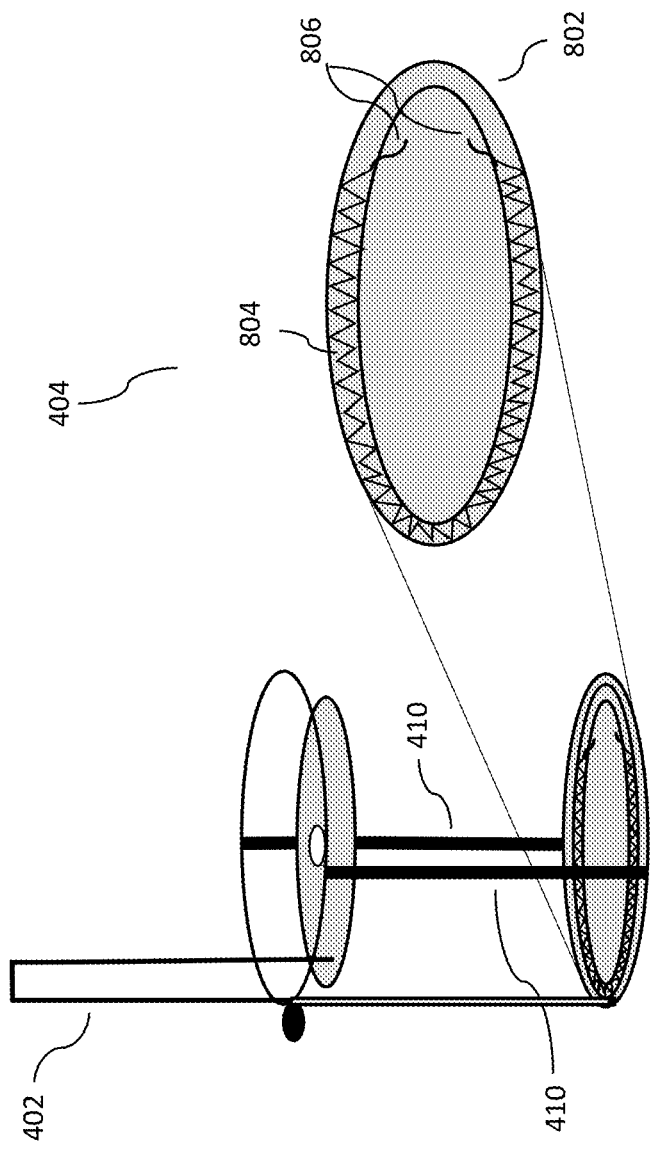
FIG. 8 depicts a schematic diagram of the base assembly of the main body subsystem of the apparatus in accordance with an embodiment of the current invention.

FIG. 8 depicts a schematic diagram of the base subsystem 404 of the apparatus in accordance with an embodiment of the current invention. The subsystem 404 comprises a disc 802, a spring 804, and one or more latches 806. The disc 802 has a short wall (not shown) around the periphery of the disc 802 and outside of the spring 804 and another short wall (not shown) around the periphery of the disc 802 and inside of the spring 804. The spring 804 is held in place by the two walls. Alternatively, the spring 804 is held in place inside a tube (not shown) placed around the edge of the disc 802. Two latches 806 are attached at the two ends of the spring 804. When the container 210 is pushed for its insertion into the main body subsystem 240, the outer wall of the container 210 pushes the latches 806 causing the spring to be compressed and making the opening between the latches wider for the container 210 to be fully inserted into the main body subsystem 240. When the container is fully inserted into the main body subsystem, the latches 806 hold the container 210 securely into the main body subsystem 240. The disc 802 can have a hole in the middle of the disc to reduce the amount of material used for the base subsystem 404.

The spring 804 and a tube (not shown) holding the spring 804 can be placed at another location above the disc 802. In this embodiment, the spring and the tube are attached to the posts 410. For example, the spring 804 and the tube (not shown) can be placed in the middle section of the posts 410 so the container 210 is held more securely.

Figure 9:
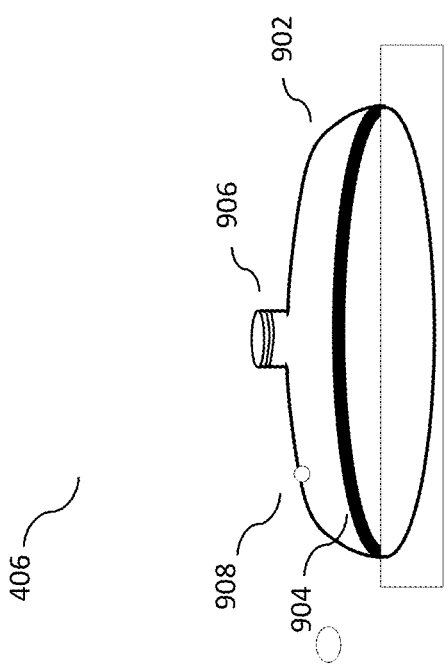
FIG. 9 depicts a schematic diagram of the lid assembly of the main body subsystem of the apparatus in accordance with an embodiment of the current invention

FIG. 9 depicts a schematic diagram of the lid subsystem 406 of the main body subsystem 240 in accordance with an embodiment of the current invention. The subsystem 406 comprises a lid 902. The lid 902 is open in the bottom part and it has a thread (not shown) on the inside of the bottom part so it can be threaded onto the container 210 for the operation of the apparatus. The lid subsystem 406 includes a narrow neck 906 with a thread on the outside of its top part. The nozzle 270 is threaded onto the thread on the neck 906 for the operation of the apparatus. The lid subsystem 406 has a hole 908. The right-hand side arm of the U-shaped rod 602 goes through the hole 908.

Figure 10:
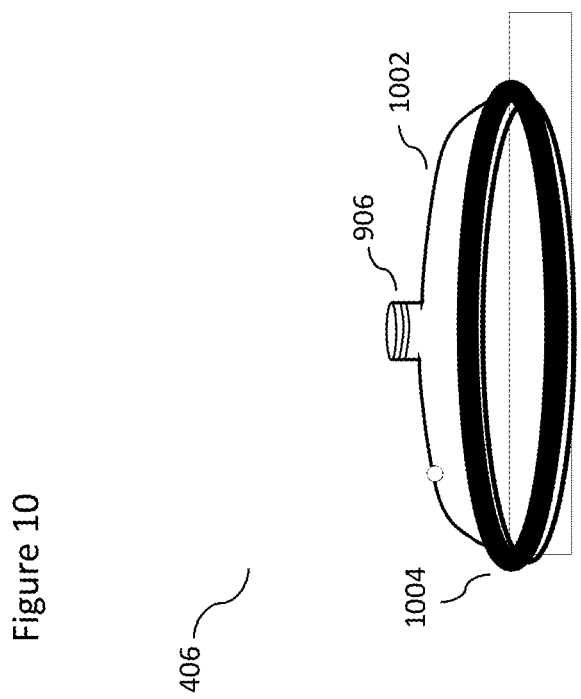
FIG. 10 depicts a schematic diagram of the lid subassembly of the main body subsystem of the apparatus in accordance with another embodiment of the current invention.

FIG. 10 depicts a schematic diagram of the lid subsystem 406 in accordance with another embodiment of the current invention. The lid subsystem 406 comprises a lid 1002 and a ring device 1004. The ring device 1004 is loosely held by a notch (not shown) at the bottom of the lid 1002. The ring device 1004 has a thread (not shown) on the inside of the bottom part of the ring device 1004. When the ring device 1004 is threaded onto the thread of the container subsystem 312, the lid subsystem 406 is securely attached to the container. In another variation of this embodiment, the lid also has a thread (not shown) on the outside of its bottom part. When the ring device is threaded onto the container subsystem 312, the ring device 1002 threads both the container 312 and the lid 1002 so the container 312 and the lid 1002 are securely attached to each other by the ring device 1004.

Figure 11:
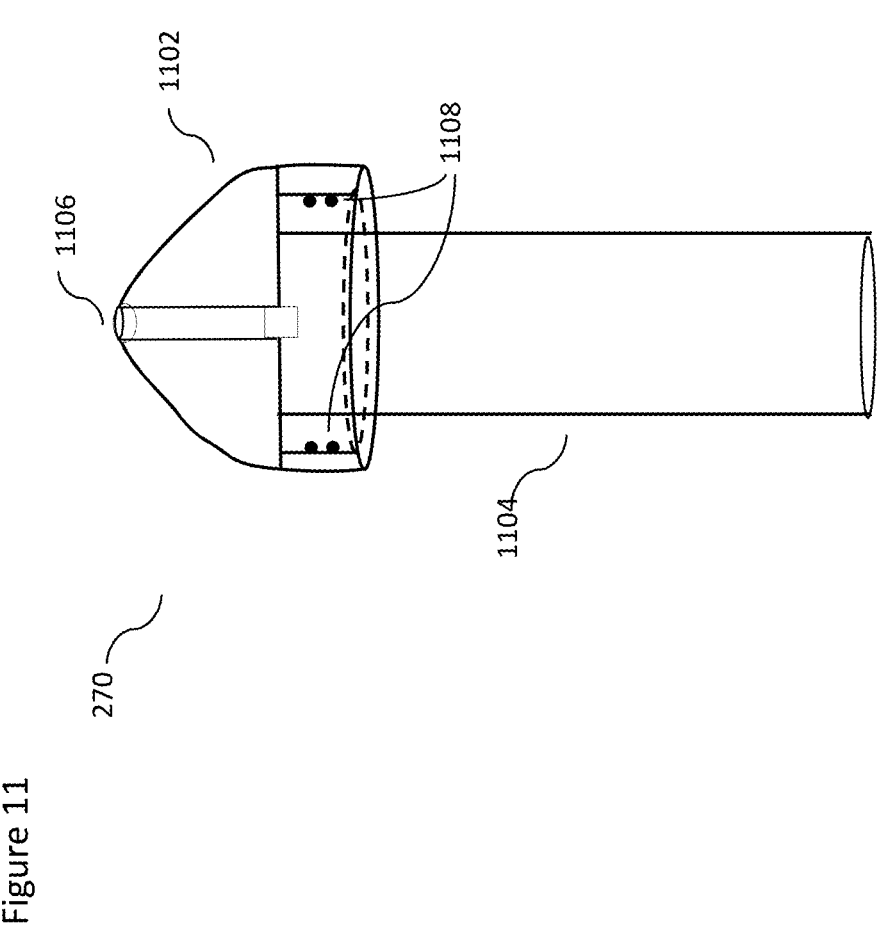
FIG. 11 depicts a schematic diagram of the nozzle assembly of the device in accordance with the current invention.

FIG. 11 depicts a schematic diagram of the nozzle 270 of the apparatus in accordance with an embodiment of the current invention. The nozzle 270 comprises a nozzle head 1102 and a tube 1104. The nozzle head 1102 is attached to the tube 1104 at the top part of the tube 1104. The tube is hollow as shown. The top of the head 1102 is protruded in a convex manner for it to fit snugly onto an opening such as a nasal opening for nasal irrigation application of the apparatus. The head 1102 has a thread 1108 on the inside of the head so it can be threaded onto the neck 906 of the lid subsystem 406. The head 1102 has an opening 1106 that is open into the tube 1104.

Figure 12:
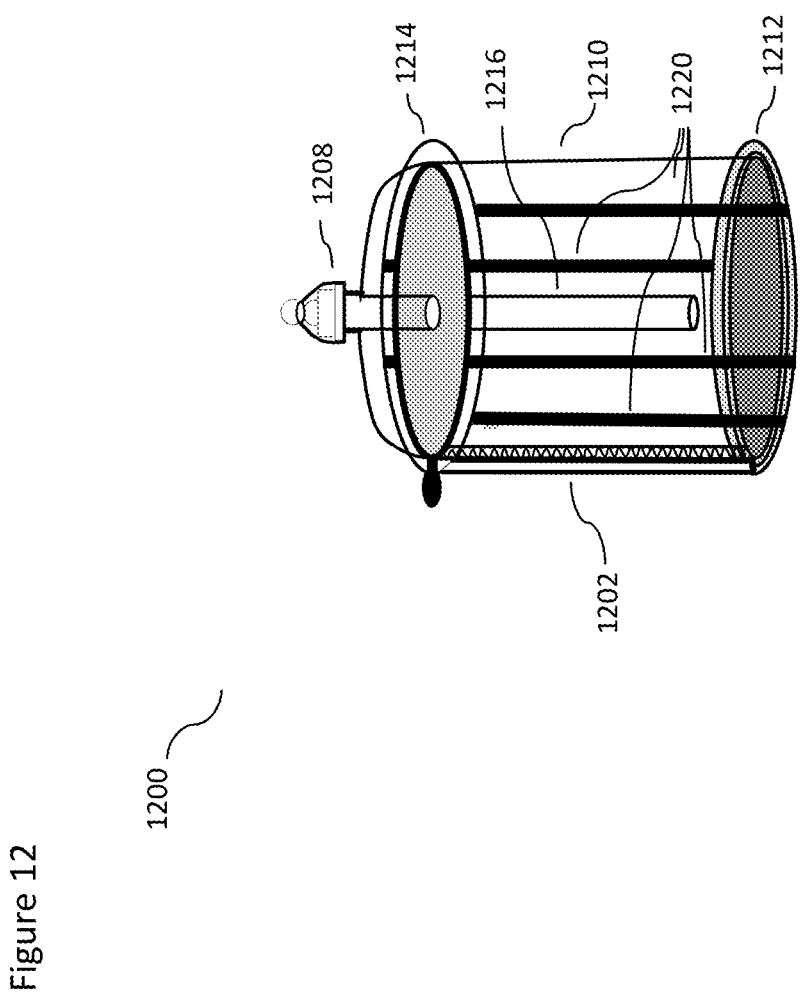
FIG. 12 depicts a schematic diagram of a liquid dispensing apparatus in accordance with another embodiment of the current invention.

FIG. 12 depicts a schematic diagram of the salient components of a liquid dispensing apparatus generally designated as 1200 in accordance with another embodiment of the current invention. The apparatus comprises a main body subsystem 1202, a container subsystem 1210, and a nozzle 1208. The container subsystem 1210 filled with liquid is dropped into the main body subsystem 1202 vertically from the top of the main body subsystem; the nozzle 1208 is threaded onto the neck of the container subsystem 1210 when liquid is to be dispensed from the container by pushing a button on the container subsystem 1210 of the apparatus 1200.

The main body subsystem 1202 comprises a base 1212 at the bottom and a ring 1214 at the top of the main body subsystem 1202, wherein the base and the ring are securely held by posts 1220.

Figure 13:
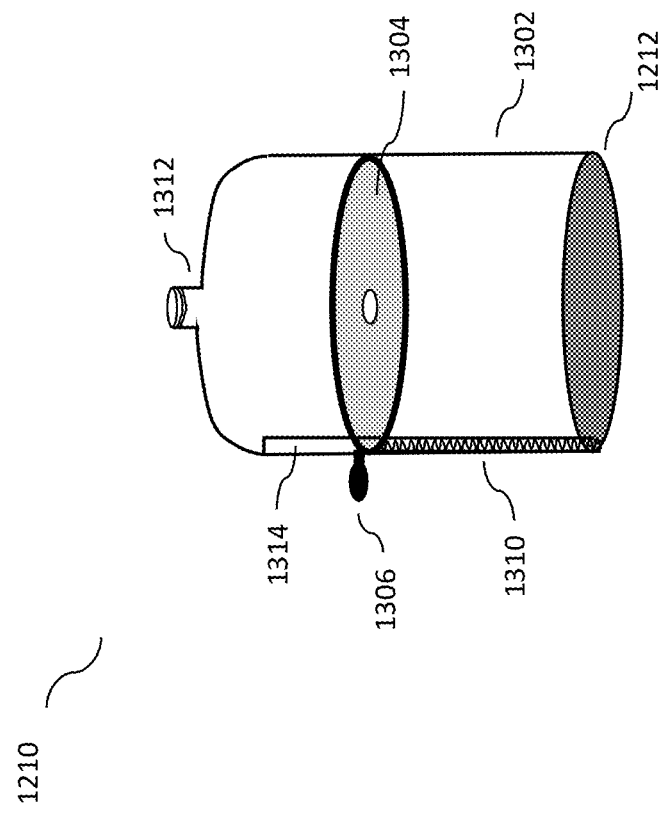
FIG. 13 depicts a schematic diagram of a container in accordance with another embodiment of the current invention.

FIG. 13 depicts a schematic diagram of the salient components of the container subsystem 1210 in accordance with an embodiment of the current invention. The container subsystem 1210 comprises a container 1302, a plunger disc 1304, a button 1306, a compressible device 1310, and a neck 1312. The neck 1312, an integral part of the container 1302, has a thread on the outside for the nozzle 1208 to be threaded on to the container 1302. The disc 1304 has a hole in the middle so the disc 1304 can slide through a tube of the nozzle 1208 in a watertight manner. The hole can be fitted with a rubber ring for making it watertight. The button 1306 is securely attached to the edge of the disc 1304. The button 1306 is also securely attached to the top part of the compressible device 1310. The container incorporates a vertical slit 1314 through which the compressible device 1310 moves up or down in a watertight manner when the button 1306 is pushed up or down.

The compressible device 1310 is made of a compressible material such as rubber or leather. The compressible device 1310 is held onto one or two posts (not shown) mounted in the vertical slit 1314. The compressible device 1310 is attached to the button 1306 and the base 1212 of the container through the one or two posts. The attachment of the compressible device to the button and the bottom of the container is fixed in a manner that liquid cannot leak out from the container 1302. The attachment of the compressible device 1310 on to the two posts is flexible so it can move up or down the posts while no liquid can leak from the container. An example of the compressible device is a leather or rubber membrane to cover the slit of the container in a watertight manner. The membrane has one or two sleeves in the middle or at the two vertical edges of the membrane. The membrane is fitted on to the container 1302 by inserting the one or two sleeves on to the one or two posts mounted in the slit 1314. A spring attached to the button at the top and to the base of the container at the bottom may also be provided so the button 1306 is always on the top of the container. When no spring is provided, the button needs to be pulled up manually for the device to be ready for operation.

Figure 14:
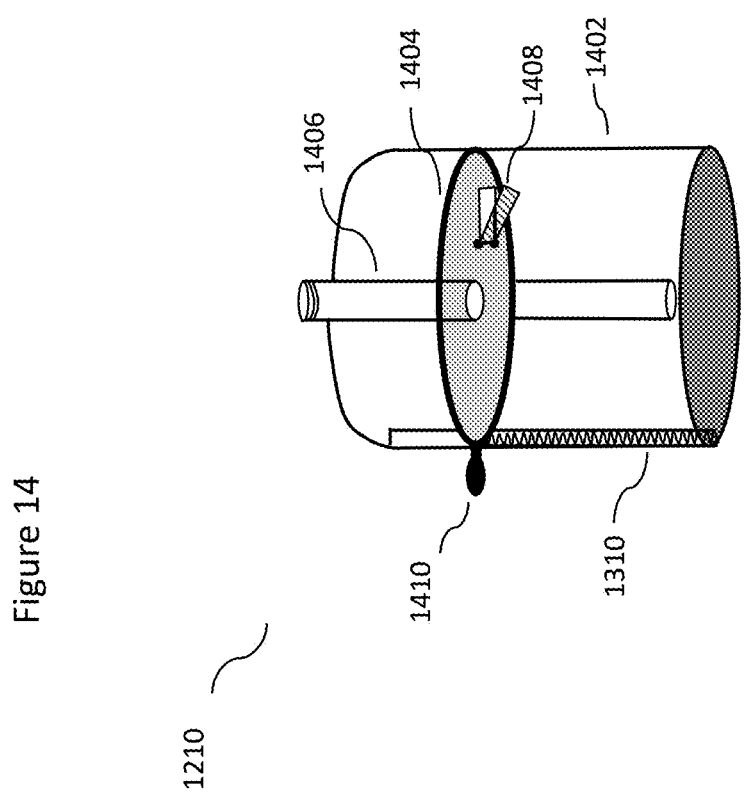
FIG. 14 depicts a schematic diagram of a container in accordance with yet another embodiment of the current invention.

FIG. 14 depicts a schematic diagram of the salient components of the container subsystem 1210 in accordance with another embodiment of the current invention. The container subsystem 1210 comprises a container 1402, a plunger disc 1404, a tube 1406, a valve 1408, a button 1410, and a compressible device 1310. The tube 1406 is attached to the top part of the container 1402 forming a neck of the container. The neck has a thread on the outside for a nozzle to be threaded onto the tube. In this embodiment, the nozzle shown in FIG. 11 does not include the tube 1104. The plunger disc 1404 includes a hole for the tube 1104 to pass through in a watertight manner. The hole can be fitted with a rubber ring for making it liquid-tight. The button 1410 is securely attached to the edge of the disc 1404. The valve 1408 opens when the disc 1404 is pushed up by pushing up the button 1410. The valve 1408 closes when the disc 1404 is pushed down. The valve allows the container 1402 to be filled with liquid when the disc 1404 is at the bottom of the of the container. When the disc 1404 is pushed up for the operation of the apparatus, the valve 1408 opens and the liquid moves below the disc 1404. Subsequently, as the button 1410 is pushed down for the operation of the apparatus, the valve 1408 closes and the liquid is squeezed up the tube 1406 and out through the nozzle 1208.

The container 210 is filled with liquid and inserted into the main body subsystem 240 through the latches 806 for it to be securely held inside the main body while the button 608 along with the rod 602 and the plunger disc 606 are held at the topmost position. The lid subsystem 406 is securely threaded onto the container 210. The nozzle 270 (without the tube 1104) is inserted into the container 210 through the lid subsystem 406 and securely threaded onto the neck of the lid subsystem 406. The apparatus is then ready for operation. When the button 608 is pushed down, the rod 602 pushes the plunger disc 606 down into the liquid filled container 210 causing the liquid to be pushed through the tube 1406 and out of the opening 1106 of the nozzle 270. The flow of liquid through the nozzle is controlled by the amount of push on the button 1410.

Figure 15:
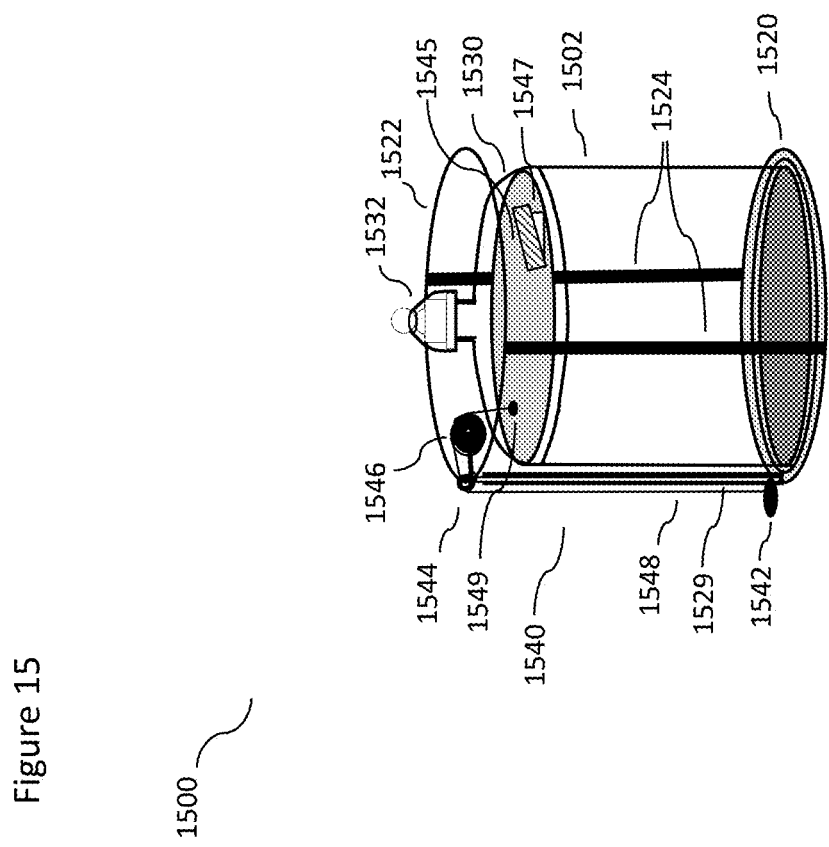
FIG. 15 depicts a schematic diagram of a liquid dispensing apparatus in accordance with another embodiment of the current invention.

FIG. 15 depicts a schematic diagram of the salient components of a liquid dispensing apparatus generally designated as 1500 in accordance with another embodiment of the current invention. The apparatus comprises a main body subsystem, a container subsystem, and an operation subsystem 1540. The container subsystem comprises a container 1502 with a thread at the outside of the top section of the container. The container 1502 filled with liquid is inserted into the main body subsystem from a side of the main body subsystem.

The main body subsystem of the apparatus according to the embodiment shown in FIG. 15 comprises a base subsystem 1520, a support ring 1522, a lid subsystem 1530, two or more support posts 1524, and a hollow structure 1529. The posts 1524 connect the base subsystem 1520 and the support ring 1522 holding the main body subsystem structure. The hollow structure 1529 is a hollow tube with a slit cut at the side for a button and a string of the operation subsystem 1540 to slide through.

The base subsystem 1520 comprises a support disc, a spring and latches like the base subsystem shown in FIG. 8 to hold the container securely in the main body subsystem of the apparatus.

The operation subsystem 1540 comprises a button 1542, two pulleys 1544 and 1546, a string 1548, a structure 1549, a plunger disc 1545, and a valve 1547. The button 1542 is attached to one end of the string 1548 and the plunger disc 1545 is attached to the other end of the string 1548 with the structure 1549. The structure 1549 can be a hook or a disc securely attached to the disc 1545. The string 1548 can also be soldered or welded on to the disc 1545. The string 1548 passes over the two pulleys 1544 and 1546. In another variation of the embodiment only one pulley is used. In another variation of the operation subsystem 1540, the string 1548 and the pulleys 1544 and 1546 are replaced with an arm lever system. In this variation, the lever is supported by a fulcrum attached to the ring 1522. One end of the lever is attached to a piston which in turn is attached to the disc 1545. When the other end of the lever is pushed down, the piston pulls the disc 1545 up achieving the same action as the pulley and string system described above.

The valve 1547 is attached to the disc 1545. The valve 1547 opens when the disc 1545 moves down the liquid filled container 1502 and closes when it is pushed up through the liquid in the container 1502.

The string 1548 and the button 1542 slide through the hollow structure 1529 when the button 1542 is pushed up or down.

The lid subsystem 1530 includes a neck to which a nozzle is attached. In this embodiment, the nozzle is an integral part of the lid subsystem. The lid subsystem 1530 includes a watertight hole through which the string 1548 slides through when the disc 1545 moves up or down. The lid subsystem includes a thread at the inside of the bottom part of the lid for the container 1502 to be threaded onto the lid. The lid subsystem 1530 is attached to the ring 1522 or to the posts 1524.

For the operation of the device 1500, the button 1542 is pushed down and the container 1502 filled with water is inserted from a side of the main body subsystem and securely held on to the base 1520. The container 1502 is threaded on to the lid 1530 by the thread of the lid or by a threaded ring device shown in FIG. 10. When the button 1542 is subsequently released, the valve 1547 opens and the disc 1545 slides down the container due to the weight of the disc 1545. An O-ring may be inserted at the periphery of the disc 1545 for the disc to move in the container 1502 in a watertight manner. If the O-ring is tight, then the weight of the disc 1545 may not be enough for it to slide down the container. In that case, the O-ring may be designed so that it is tight when the disc 1545 moves up the container 1502 but loose when it moves down the container 1502. Alternatively, a spring may be attached between the neck of the lid subsystem and the plunger disc 1545. The spring, when not pushed up by the button 1542 by its being pushed down, pushes down the plunger disc 1545 to the bottom of the container 1502 through the liquid in the container.

When the disc 1545 is at the bottom of the container 1502, the button 1542 is at the top of the structure 1529. As the button 1542 is pushed down, the disc 1545 moves up and the valve 1547 closes resulting in the liquid in the container to be pushed out of the container through the nozzle 1532 for the operation of the apparatus.

It is to be understood that the above-described embodiments are merely illustrative of the present invention and that many variations of the above-described embodiments can be devised by those skilled in the art without departing from the scope of the invention. For example, in this Specification, numerous specific details are provided in order to provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments.

It is understood that the various embodiments shown in the Figures are illustrative and are not necessarily drawn to scale. Reference throughout the specification to "first embodiment" or "second embodiment" or "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "first embodiment," "second embodiment," "third embodiment," "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed is:

1. A nasal irrigation apparatus comprising: a liquid container, a main body subsystem, an operation subsystem, and a nozzle;
   wherein the main body subsystem allows the liquid container to be inserted into and removed out of the main body subsystem;
   wherein the liquid container is held into the main body subsystem substantially securely when the liquid container is threaded onto the main body subsystem for operation of the nasal irrigation apparatus;
   wherein the operation subsystem comprises a button, a rod, and a plunger disc;
   wherein the nozzle comprise a nozzle head to fit snugly onto a nasal opening and a nozzle tube;
   wherein the nozzle tube passes through a hole in the plunger disc;
   wherein the plunger disc is moved down inside the liquid container over the nozzle tube when the button is pushed down to operate the nasal irrigation apparatus; and
   wherein, the main body subsystem having been coupled with the liquid container, the nasal irrigation apparatus dispenses at least a portion of a liquid in the liquid container through the nozzle head in a first direction when the nasal irrigation apparatus is operated by pushing the button a second direction substantially opposite to the first direction.

2. The nasal irrigation apparatus of claim 1 wherein the liquid container is made of one of a ceramic material and a glass material.

3. The nasal irrigation apparatus of claim 1 wherein a horizontal cross-section of the liquid container is one of a circular shape, an elliptical shape, and a polygonal shape.

4. The nasal irrigation apparatus of claim 1 wherein the main body subsystem comprising: a base subsystem, a lid subsystem, a support ring, and a first support structure;
   wherein the first support structure couples the base subsystem and the support ring; and
   wherein the first support structure includes at least one opening through which the liquid container is inserted into or removed out of the main body subsystem.

5. The nasal irrigation apparatus of claim 4 wherein the first support structure comprises a set of posts.

6. The nasal irrigation apparatus of claim 4 wherein the first support structure comprises a plate having a shape to substantially conform the shape of the first support structure with a shape of the support ring and with a shape of an outer edge of the base subsystem.

7. The nasal irrigation apparatus of claim 4 wherein the base subsystem comprising: a base disc, a peripheral structure, a spring, and one or more latches;
   wherein the peripheral structure is either a tube or two concentric walls;
   wherein the peripheral structure is attached either to a periphery of the base disc or to the first support structure;
   wherein the spring is held inside the peripheral structure;
   wherein at least one of the one or more latches is attached to one of two ends of the spring; and
   wherein the spring contracts when the liquid container is pushed through the one or more latches allowing the liquid container to be inserted into the main body subsystem; and
   wherein the liquid container is held substantially securely into the main body subsystem by the spring when the liquid container is fully inserted into the main body subsystem.

8. The nasal irrigation apparatus of claim 4 wherein the lid subsystem comprising a lid;
   wherein the lid comprises a first thread on an inside of the lid matching a second thread on an outside of the liquid container allowing the lid to be threaded onto the liquid container;
   wherein the lid comprises a neck at a top part of the lid;
   wherein the neck comprises a third thread at an outside of the neck;
   wherein the third thread is matching with a fourth thread on the nozzle allowing the nozzle to be threaded securely onto the lid; and
   wherein the lid comprises a hole to allow the rod to pass through the hole.

9. The nasal irrigation apparatus of claim 4 wherein the lid subsystem comprising a lid;
   wherein the lid comprises a first thread on an inside of the lid matching a second thread on an outside of the liquid container allowing the lid to be threaded onto the liquid container;
   wherein the lid comprises a neck at a top part of the lid;
   wherein the nozzle is permanently attached to neck of the liquid container; and
   wherein the lid comprises a hole to allow the string to pass through.

10. The nasal irrigation apparatus of claim 4 wherein the lid subsystem comprising: a lid and a coupling ring device;
    wherein the coupling ring device is loosely coupled with the lid at an outer side of the lid when not threaded;
    wherein the coupling ring device includes a first thread on an inner side of the coupling ring device matching a second thread on an outer side of the liquid container allowing the coupling ring device to be threaded onto the liquid container; and
    wherein the coupling ring device couples the lid and the liquid container substantially securely when the coupling ring device is threaded onto the liquid container.

11. The nasal irrigation apparatus of claim 1 wherein the operation subsystem further comprising a second support structure;
    wherein the rod is substantially U-shaped;
    wherein the second support structure comprises either a hollow tube with a slit cut on a side of the hollow tube or a post;
    wherein a portion of the rod moves up or down through the second support structure when the button is pushed;
    wherein the rod couples the button at one end of the rod and the plunger disc at the other end of the rod; and wherein the plunger disc is of a shape and size to substantially fit and to slide through the liquid container in a liquid-tight manner when the plunger disc moves through the liquid container.

12. The nasal irrigation apparatus of claim 11 wherein the second support structure further comprising a spring and a latch;
   wherein the spring connects the button and the base subsystem at two ends of the spring;
   wherein the spring is held down by the latch when the button is pushed substantially to a bottom of the second support structure and subsequently released; and
   wherein the latch releases the spring when the button is pushed upwards.

13. The nasal irrigation apparatus of claim 1 wherein the nozzle head includes a first thread on an inner side of the nozzle head;
   wherein the first thread is matching with a second thread on the lid subsystem; and
   wherein the nozzle head couples with the lid subsystem securely when the nozzle is threaded onto the lid subsystem.

14. A method for dispensing a liquid from a nasal irrigation device comprising:
   inserting a container at least partially filled with the liquid into a main body subsystem of the nasal irrigation device to be securely held in the nasal irrigation device;
   threading the container onto the main body subsystem to substantially secure the container for operation of the liquid dispensing apparatus;
   threading a lid onto the container to securely attach the lid onto the container;
   threading a nozzle onto the lid to securely attach the nozzle onto the lid, wherein the nozzle comprises a nozzle head to fit snugly onto a nasal opening and a nozzle tube, wherein the nozzle tube passes through a hole in a plunger disc; and
   pushing a button down to move the plunger disc down inside the container over the nozzle tube to operate the nasal irrigation device;
   wherein pushing the button of the nasal irrigation device comprises pushing the button in a first direction to dispense at least a portion of the liquid in the container through the nozzle in a second direction substantially opposite to the first direction, wherein an operation subsystem comprises the button, a rod, and the plunger disc.

15. The method of claim 14 further comprising:
unthreading the lid from the container; unthreading the nozzle from the lid;
pushing the button in the second direction to recouple the container from the nasal irrigation device; and removing the container out of the nasal irrigation device.

\* \* \* \* \*